(12) United States Patent
Yu et al.

(10) Patent No.: US 6,197,526 B1
(45) Date of Patent: Mar. 6, 2001

(54) POLYPEPTIDES FOR BINDING HUMAN FACTOR VIII AND FRAGMENTS OF HUMAN FACTOR VIII

(75) Inventors: Jinan Yu; M. Daniel Potter, both of Acton; Brian D. Kelley, Medford; Jeffrey S. Deetz, Melrose; James Edward Booth, Andover, all of MA (US)

(73) Assignees: Dyax Corp.; Genetics Inst., both of Cambridge, MA (US)

( * ) Notice: Subject to any disclaimer, the term of this patent is extended or adjusted under 35 U.S.C. 154(b) by 0 days.

(21) Appl. No.: 09/224,785

(22) Filed: Jan. 4, 1999

(51) Int. Cl.[7] .............................. G01N 33/53; C12Q 1/70; C12N 9/00; C07K 1/00; A61K 38/00
(52) U.S. Cl. .................... 435/7.1; 435/5; 435/7.4; 435/13; 435/183; 530/412; 530/413; 530/324; 530/327; 530/344; 436/501; 436/518; 514/14; 514/15
(58) Field of Search .................... 530/327, 324, 530/344, 412, 413; 435/13, 5, 7.1, 7.4, 183; 436/501, 518; 514/14, 15

(56) References Cited

U.S. PATENT DOCUMENTS

| | | |
|---|---|---|
| 4,749,780 | 6/1988 | Andersson et al. . |
| 4,757,006 | 7/1988 | Toole, Jr. et al. . |
| 4,868,112 | 9/1989 | Toole, Jr. et al. . |
| 4,877,614 | 10/1989 | Andersson et al. . |
| 5,223,409 | 6/1993 | Ladner et al. . |
| 5,661,008 | 8/1997 | Almstedt et al. . |
| 5,817,752 | 10/1998 | Yu et al. . |
| 5,994,310 | 11/1999 | Buettner et al. . |

FOREIGN PATENT DOCUMENTS

WO 97/46251  12/1997  (WO) .

OTHER PUBLICATIONS

Houghten, *Proc. Natl. Acad. Sci. USA*, 82: 5131 (1985).
Kelley et al., *Genetic Engineering Principles and Methods*, (Setlow, J.K., ed.), Plenum Press, NY., 12: 1–19 (1990).
Lind et al., *Euro. J. Biochem.*, 232:19–27 (1995).
Merrifield, *J. Am. Chem. Soc.*, 85:2149 (1963).
Stewart et al., *Solid–Phase Peptide Synthesis*, W.H. Freeman Co., San Francisco (1989). pp. ix–xi.
White, *Blood: Principles and Practices of Hematology*, (Handin et al., eds.), J.B. Lippencott Co., Philadelphia (1995). pp. 1151–1174.
Kay et al., *Phage Display of Peptides and Proteins: A Laboratory Manual*, Academic Press, Inc., San Diego (1996). pp. V–XII.
Bahou et al., *J. Clin. Invest.*, 84: 56–61 (1989).
Jorieux et al., *Brit. J. of Haematology*, 87: 113–118 (1994).
Ware et al., *Proc. Natl. Acad. Sci. USA*, 85: 3165–3169 (1988).

*Primary Examiner*—Christina Y. Chan
*Assistant Examiner*—Karen Clemens
(74) *Attorney, Agent, or Firm*—Leon R. Yankwich; David G. O'Brien

(57) ABSTRACT

Methods for detecting human factor VIII or factor VIII-like polypeptides in and isolating it from solutions such as blood or conditioned media are disclosed, together with reagents suitable for the purpose comprising binding moieties that recognize human factor VIII and/or a factor VIII-like polypeptide and form a binding complex therewith. Preferred polypeptide binding moieties are particularly disclosed.

21 Claims, No Drawings

POLYPEPTIDES FOR BINDING HUMAN FACTOR VIII AND FRAGMENTS OF HUMAN FACTOR VIII

FIELD OF THE INVENTION

The present invention relates to the field of protein isolation and purification. Specifically, the present invention relates to the identification, isolation and synthesis of binding molecules that bind to factor VIII and/or factor VIII-like polypeptides. Such binding molecules are useful for the detection and purification of factor VIII and factor VIII-like polypeptides from solutions containing them.

BACKGROUND

Classical hemophilia A is the result of a chromosome X-linked deficiency of blood plasma coagulation factor VIII and affects almost exclusively males with a frequency of about 1 case per 10,000. The X-chromosome defect is transmitted by female carriers who do not themselves have the disease. Factor VIII is also known as antihemophilic factor (AHF), hemophilic factor A, platelet cofactor, thromboplastinogen, thrombocytolysin, and antihemophilic globulin (AHG). The designation "factor VIII:C" is used to indicate that it is the compound that affects clotting. Factor VIII is a high molecular weight protein of 280 kDa and is composed of two polypeptide chains of 200 kDa and 80 kDa, respectively. Andersson et al., *Proc. Natl. Acad. Sci. U.S.A.*, 83:2979–2973 (1986). These chains are held together by a metal ion bridge.

The principal symptom of hemophilia A is bleeding without clotting or coagulation. Prior to the discovery that administration of factor VIII concentrates could ease the symptoms of an individual diagnosed with the disease, the average life expectancy of a sufferer was about 20 years.

Until recent years, the major source of factor VIII for therapeutic purposes was normal blood plasma; however factor VIII isolated by this method, while of some use, has several important disadvantages. For instance, factor VIII isolated from blood plasma is fairly impure, typically having a specific activity of less than 2 units factor VIII/mg protein and an overall factor VIII content of less than 1%. Additionally, the purification process is expensive because the starting material, i.e., human plasma, is expensive. Many precautions must also be taken to decrease the risk of transmitting infectious agents to the patient. For example, human immunodeficiency virus (HIV), Hepatitis B virus, Hepatitis C virus and other disease-causing agents are commonly detected in donated blood. Another disadvantage of using factor VIII obtained by this method is that approximately one-tenth of the patients with severe hemophilia A develop antibodies against factor VIII, making the disease difficult to treat.

Research efforts have focused on the development of methods for creating and isolating highly purified, biologically active factor VIII in full-length and derivative forms. Advantages of a highly purified protein include reduced levels of extraneous proteins in the therapeutic mix as well as a decreased likelihood of the presence of infectious agents. A more purified form of factor VIII may also be administered in smaller doses, possibly reducing the risk of developing anti-factor VIII antibodies, as lower doses would be less challenging to the immune system.

Significant steps have been taken toward the recombinant production of factor VIII beginning with the isolation of biologically active factor VIII fragments. See, Andersson et al., U.S. Pat. No. 4,749,780; Andersson et al., U.S. Pat. No. 4,877,614. The gene encoding the full-length human factor VIII protein was isolated by taking advantage of its sequence homology with porcine factor VIII. See, Toole et al., U.S. Pat. No. 4,757,006. Toole et al. also report the expression of human and porcine protein having factor VIII:C procoagulant activity.

However, severe side effects involving the production of anti-factor VIII antibodies still exist with the administration of the protein isolated from both human and non-human sources. Antibodies that react with human factor VIII:C are also known to react, to a certain extent, with factor VIII:C from other species, and porcine factor VIII itself is antigenic in humans. Also, non-hemophiliacs can develop or acquire the disease when their immune systems become sensitized to factor VIII:C.

As a possible solution to this problem, a truncated, lower molecular weight protein exhibiting procoagulant activity has been designed. See, Toole, U.S. Pat. No. 4,868,112. Toole reported an alternative method of treatment with lower molecular weight porcine factor VIII of approximately 2000 amino acids exhibiting similar procoagulant activity as full-length factor VIII. Evidently, the removal of certain amino acids and up to 19 of the 25 possible glycosylation sites, reduced the antigenicity of the protein and thereby the likelihood of developing anti-factor VIII antibodies. However, one difficulty with the development of recombinant factor VIII is achieving production levels in sufficiently high yields.

Recently, deleted factor VIII cDNA molecules coding for recombinant factor VIII derivatives, which were likely to give sufficiently high yields of a biologically active recombinant factor VIII protein for use in an industrial process for a pharmaceutical preparation have been developed. See, Almstedt et al., U.S. Pat. No. 5,661,008. Almstedt et al. designed a modified factor VIII derived from a full-length factor VIII cDNA, that, when expressed in animal cells, produced high levels of a factor VIII-like protein with factor VIII activity. The protein consisted essentially of two polypeptide chains derived from human factor VIII, the chains having molecular weights of 90 kDa and 80 kDa, respectively.

According to the Almstedt et al. process, the factor VIII cDNAs are assembled into transcription units and introduced into a suitable host system for expression. The cell lines can be grown on a large scale in suspension culture or on solid support. The protein produced in the culture medium is then concentrated and purified. The final active protein is made up of amino acids 1 to 743 and 1638 through 2332 of human factor VIII This polypeptide sequence is commercially known as rFVIII-SQ or REFACTO®. See also, Lind et al., *Euro. J. Biochem.*, 232:19–27 (1995). Other forms of truncated FVIII can also be constructed in which the B-domain is generally deleted. In such embodiments, the amino acids of the heavy chain, consisting essentially of amino acids 1 through 740 of human Factor VIII and having a molecular weight of approximately 90 kD are connected to the amino acids of the light chain, consisting essentially of amino acids 1649 to 2332 of human Factor VIII and having a molecular weight of approximately 80 kD. The heavy and light chains may be connected by a linker peptide of from 2 to 15 amino acids, for example a linker comprising lysine or arginine residues, or alternatively, linked by a metal ion bond.

Currently, there is a need in the field for efficient and cost-effective methods for obtaining purified, active factor VIII directly from various solutions such as blood or cell culture supernatants.

The present invention provides new materials and methods for identifying, isolating, and purifying factor VIII and factor VIII-like proteins, including REFACTO®, from a solution that contains such proteins, in an active form. The factor VIII binding molecules of the present invention exhibit high affinity for factor VIII and factor VIII-like peptides. The current invention thus provides a cost-effective means for rapid purification of commercial quantities of proteins useful in the treatment of hemophilia A.

SUMMARY OF THE INVENTION

Accordingly, it is an object of the present invention to provide novel binding molecules for factor VIII and factor VIII-like proteins. Preferred binding molecules of the present invention exhibit not only distinct characteristics for binding of the target factor VIII polypeptides but also specific and desirable characteristics for release (elution) of the target polypeptides. Especially preferred binding molecules according to the invention are short polypeptide sequences, characterized by a stable loop structure.

A preferred method is disclosed herein for isolation of binding molecules according to the invention by employing phage display technology. The phage display method of the current invention is useful for identifying families of polypeptide binding molecules, and using this technique several binding peptides exhibiting high affinity for factor VIII and factor VIII-like peptides have been identified and isolated. Such binding peptides are useful for identifying, isolating and purifying factor VIII and factor VIII-like polypeptides from a solution.

The most preferred binding molecules specific for factor VIII and factor VIII-like peptides isolated by the phage display method of the present invention are polypeptides characterized by a loop structure formed as a result of a disulfide bond between two cysteine residues located at the positions disclosed in SEQ ID NO: 1, SEQ ID NO: 2, and SEQ ID NO: 3. Specific polypeptide binding molecules according to the present invention include polypeptides comprising amino acid sequences of the following general formulas:

I. $X_1$-$X_2$-Cys-$X_3$-$X_4$-$X_5$-$X_6$-$X_7$-Cys-$X_8$-$X_9$ (SEQ ID NO: 1), wherein $X_1$ is Arg, Phe, His or Pro; $X_2$ is Ser, Gly, Leu or His; $X_3$ is Gly, Asn, Ile or Ser; $X_4$ is Ser, Trp or Gly; Xs is Trp, Ile, Leu or Val; $X_6$ is Phe, Trp or Ser; $X_7$ is Pro or Phe; $X_8$ is Ser, Leu, Pro or Phe; $X_9$ is Ala, Phe, Leu or His;

II. $X_{10}$-$X_{11}$-Cys-$X_{12}$-$X_{13}$-Trp-$X_{14}$-$X_{15}$-Pro-Cys-$X_{16}$-$X_{17}$ (SEQ ID NO: 2), wherein $X_{10}$ is Arg or His; $X_{11}$ is Ala, Arg, Gly, Leu or Pro; $X_{12}$ is Gly or Phe; $X_{13}$ is Ala or Ser; $X_{14}$ is Leu or Phe; $X_{15}$ is Arg, Asn or His; $X_{16}$ is Ala, Asp, His, Leu, Phe, Pro, or Tyr; $X_{17}$ is Ala, Arg, Asn, Asp, or His; and III. Phe-Cys-$X_{18}$-Val-$X_{19}$-$X_{20}$-Phe-$X_{21}$-His-Cys-$X_{22}$ (SEQ ID NO: 3), wherein $X_{18}$ is His or Trp; Xlg is His or Phe; $X_{20}$ is Ala, Asn, His, or Pro; $X_{21}$ is Ala, Asn, Asp, Gln, His, Leu, Ser, or Val; $X_{22}$ is Ala, Asp, His, Leu, Phe, or Ser.

In addition, it is also envisioned that the phage display method of the current invention can also be used to isolate additional families of binding molecules specific for factor VIII and factor VIII-like polypeptides.

The most preferred binding molecules for isolation and/or purification of factor VIII and factor VIII-like polypeptides, including especially REFACTO®, mentioned above, from a solution include the following polypeptides:

His-Ser-Cys-Gly-Ser-Trp-Leu-Phe-Pro-Cys-Phe-Ala (SEQ ID NO: 4);
Phe-Gly-Cys-Ser-Trp-Leu-Phe-Pro-Cys-Pro-Phe (SEQ ID NO: 5);
Pro-His-Cys-Asn-Trp-Leu-Phe-Pro-Cys-Ser-Leu (SEQ ID NO: 6);
Arg-Leu-Cys-Ser-Trp-Ile-Ser-Pro-Cys-Ser-Ala (SEQ ID NO: 7);
Phe-His-Cys-Ile-Gly-Val-Trp-Phe-Cys-Leu-His (SEQ ID NO: 8);
Arg-Leu-Cys-Ser-Trp-Val-Ser-Pro-Cys-Ser-Ala (SEQ ID NO: 9);
His-Pro-Cys-Gly-Ser-Trp-Leu-Arg-Pro-Cys-Leu-His (SEQ ID NO: 10);
Arg-Gly-Cys-Gly-Ser-Trp-Leu-Arg-Pro-Cys-Leu-Asp (SEQ ID NO: 1);
His-Pro-Cys-Gly-Ser-Trp-Leu-His-Pro-Cys-Ala-Ala (SEQ ID NO: 12);
His-Pro-Cys-Gly-Ser-Trp-Phe-Asn-Pro-Cys-Ala-His (SEQ ID NO: 13);
His-Pro-Cys-Gly-Ser-Trp-Phe-Arg-Pro-Cys-Phe-His (SEQ ID NO: 14);
His-Ala-Cys-Gly-Ser-Trp-Phe-Arg-Pro-Cys-His-Ala (SEQ ID NO: 15);
His-Leu-Cys-Gly-Ala-Trp-Phe-Arg-Pro-Cys-Asp-Ala (SEQ ID NO: 16);
His-Leu-Cys-Phe-Ala-Trp-Phe-Arg-Pro-Cys-Asp-Ala (SEQ ID NO: 17);
His-Gly-Cys-Gly-Ala-Trp-Phe-Arg-Pro-Cys-His-Ala (SEQ ID NO: 18);
His-Pro-Cys-Gly-Ala-Trp-Phe-Asn-Pro-Cys-Pro-Arg (SEQ ID NO: 19);
His-Pro-Cys-Gly-Ala-Trp-Leu-Arg-Pro-Cys-Tyr-Asn (SEQ ID NO: 20);
His-Arg-Cys-Gly-Ser-Trp-Leu-His-Pro-Cys-Leu-Ala (SEQ ID NO: 21);
Phe-Cys-Trp-Val-Phe-Ala-Phe-Asp-His-Cys-His (SEQ ID NO: 22);
Phe-Cys-Trp-Val-His-Pro-Phe-Ala-His-Cys-Leu (SEQ ID NO: 23);
Phe-Cys-His-Val-Phe-His-Phe-Ser-His-Cys-Asp (SEQ ID NO: 24);
Phe-Cys-Trp-Val-Phe-Ala-Phe-Asp-His-Cys-His (SEQ ID NO: 25);
Phe-Cys-Trp-Val-Phe-Asn-Phe-Ser-His-Cys-Ser (SEQ ID NO: 26);
Phe-Cys-Trp-Val-Phe-Pro-Phe-Asn-His-Cys-Asp (SEQ ID NO: 27);
Phe-Cys-Trp-Val-Phe-Pro-Phe-Asn-His-Cys-Ser (SEQ ID NO: 28);
Phe-Cys-Trp-Val-Phe-Pro-Phe-Gln-His-Cys-Ala (SEQ ID NO: 29);
Phe-Cys-Trp-Val-Phe-Pro-Phe-His-His-Cys-Phe (SEQ ID NO: 30);

Phe-Cys-His-Val-Phe-Asn-Phe-Val-His-Cys-Ser (SEQ ID NO: 31);

Phe-Cys-His-Val-Phe-Pro-Phe-Leu-His-Cys-Asp (SEQ ID NO: 32);

Solutions from which factor VIII and factor VIII-like polypeptides may be isolated and purified from include, but are not limited to, blood, blood fractions, and recombinant cell culture supernatants containing factor VIII or a factor VIII-like polypeptide produced and secreted by the recombinant host cell.

In another embodiment, the present invention provides a method for identifying and isolating factor VIII binding molecules via phage display technology. More specifically, the factor VIII and factor VIII-like binding molecules having specific and predetermined binding and elution characteristics may be selected from a binding molecule library, such as a phage display library, by a method comprising:

(a) selecting a first solution condition (i.e., the binding conditions) at which it is desired that a binding molecule should exhibit an affinity for factor VIII or a factor VIII-like polypeptide, forming an affinity complex;

(b) selecting a second solution condition (i.e., the release conditions) at which it is desired that the binding molecule will dissociate from the factor VIII or factor VIII-like polypeptide, wherein the second solution condition is different in some respect (e.g., temperature, pH, solvent concentration, etc.) from the first solution condition;

(c) providing a library of analogues of a parental factor VIII binding domain, wherein each analogue differs from said parental binding domain by variation of the amino acid sequence at one or more amino acid positions within the domain;

(d) contacting said library of analogues with factor VIII or a factor VIII-like polypeptide at the first solution condition under conditions suitable to form a complex between the binding molecule and a factor VIII or factor VIII-like polypeptide;

(e) removing from the solution the unbound members (analogues) of the binding domain library;

(f) subjecting the factor VIII or factor VIII-like polypeptide complexes that remain from step (e) to the second solution condition for dissociation of some of the binding molecule/factor VIII (or factor VIII-like polypeptide) complexes;

(g) recovering the binding analogues released under the second solution condition, wherein the recovered analogues identify isolated factor VIII or factor VIII-like binding molecules.

Optionally, the above procedure can include additional release condition steps, i.e., optionally subjecting the factor VIII or factor VIII-like polypeptide complexes that remain from step (f) to a third solution condition to dissociate other remaining complexes, which may be collected in a fraction separate from the factor VIII binding molecules released under the second solution conditions. Such a step, if the conditions are stringent enough to dissociate all of the complexes formed in step (d), will identify solution conditions suitable for regeneration of binding matrices utilizing the binding molecules isolated according to this process.

Also included in the present invention are non-peptide binding molecules and modified polypeptides that bind factor VIII and/or factor VIII-like polypeptides. An example of these modifications is a constrained-loop peptide having paired cysteine residues that form disulfide bonds, modified at the cysteine residues by substitution of one of the cysteines with non-natural amino acids capable of condensing with the other cysteine side-chain to form a stable thioether bridge. Such cyclic thioether analogues of synthetic peptides are described in PCT publication WO 97/46251, incorporated herein by reference. Other specifically contemplated modifications include specific amino acid substitutions to lend stability or other properties without significantly affecting factor VIII binding, e.g., substitution of Glu-Pro for Asp-Pro to reduce acid lability); N-terminal or C-terminal modifications to incorporate linkers such as poly-glycine segments and alterations to include functional groups, notably hydrazide (—NH—NH$_2$) functionalities, e.g., to assist in immobilization of binding polypeptides according to this invention on solid supports.

In a further embodiment, the present invention encompasses a composition of matter comprising isolated nucleic acids, preferably DNA, encoding binding molecules of the present invention.

In another embodiment, the present invention provides a method for detecting a factor VIII or a factor VIII-like peptide in a solution suspected of containing it, comprising contacting the solution with a binding molecule according to the invention and determining whether a binding complex has formed.

A further embodiment of the present invention is a method for purification of factor VIII or a factor VIII-like polypeptide from a solution containing it, comprising the steps:

(a) contacting a solution containing factor VIII or a factor VIII-like polypeptide with a binding molecule according to this invention under solution conditions conducive to forming a binding complex comprised of factor VIII or a factor VIII-like polypeptide and the binding molecule;

(b) separating the complexes from the non-binding components of the solution;

(c) dissociating the factor VIII or factor VIII-like polypeptide from the binding molecule; and (d) collecting the dissociated, purified factor VIII or factor VIII-like polypeptide.

Also envisioned by the present invention is a method for isolating factor VIII and factor VIII-like peptides comprising:

(a) immobilizing a binding molecule according to the invention on a solid support, (b) contacting a factor VIII-containing solution or factor VIII-like polypeptide-containing solution with the solid support, (c) removing the non-binding components from the solution, and (d) eluting the factor VIII or factor VIII-like polypeptide from the solid support.

DEFINITIONS

As used herein, the term "recombinant" is used to describe non-naturally altered or manipulated nucleic acids, host cells transfected with exogenous nucleic acids, or polypeptides expressed non-naturally, through manipulation of isolated DNA and transformation of host cells. Recombinant is a term that specifically encompasses DNA molecules which have been constructed in vitro using genetic engineering techniques, and use of the term "recombinant" as an adjective to describe a molecule, construct, vector, cell, polypeptide or polynucleotide specifically excludes naturally occurring such molecules, constructs, vectors, cells, polypeptides or polynucleotides.

The term "bacteriophage" is defined as a bacterial virus containing a DNA core and a protective shell built up by the aggregation of a number of different protein molecules. The terms "bacteriophage" and "phage" are used herein interchangeably.

The term "factor VIII-like polypeptide" is used to refer to a modified or truncated form of natural factor VIII or full-length recombinant factor VIII, which factor VIII-like polypeptide retains the procoagulant properties of factor VIII. Examples of factor VIII-like polypeptides are those active factor VIII fragments and factor VIII derivatives disclosed in the Andersson et al., Toole, and Almstedt et al. patents cited above, all of which are incorporated herein by reference. The term "factor VIII target" is sometimes used below to refer collectively to factor VIII and/or factor VIII-like polypeptides contained in a solution or production feed stream.

The term "binding molecule" as used herein refers to any molecule, polypeptide, peptidomimetic or transformed cell ("transformant") capable of forming a binding complex with another molecule, polypeptide, peptidomimetic or tranformant. A "factor VIII binding molecule" is a binding molecule that forms a complex with factor VIII. Specific examples of factor VIII binding molecules are the polypeptides described herein (e.g., SEQ ID NOs: 1–32) and bacteriophage displaying any of such polypeptides. Also included within the definition of factor VIII binding molecules are polypeptides derived from or including a polypeptide having an amino acid sequence according to formula I, II or III, above, and such polypeptides which have been modified for particular results. Specific examples of modifications contemplated are C-terminal or N-terminal amino acid substitutions or polypeptide chain elongations for the purpose of linking the binding moiety to a chromatographic support or other substrate, and substitutions of pairs of cysteine residues that normally form disulfide links, for example with non-naturally occurring amino acid residues having reactive side chains, for the purpose of forming a more stable bond between those amino acid positions than the former disulfide bond. All such modified binding molecules are also considered binding molecules according to this invention so long as they retain the ability to bind factor VIII and/or factor VIII-like polypeptides.

DETAILED DESCRIPTION OF THE PREFERRED EMBODIMENTS

The present invention makes possible the highly selective detection or purification of factor VIII and/or factor VIII-like polypeptides in or from solutions containing them.

The factor VIII and factor VIII-like peptides may be produced in any known way, including chemical synthesis; production in transformed host cells; secretion into culture medium by naturally occurring cells or recombinantly transformed bacteria, yeasts, fungi, insect cells, and mammalian cells; secretion from genetically engineered organisms (e.g., transgenic mammals); or in biological fluids or tissues such as blood, plasma, etc. The solution that contains the crude factor VIII as it is initially produced (i.e., the production solution) will sometimes be referred to as the "feed stream".

Each method of producing factor VIII (or a factor VIII-like polypeptide) yields factor VIII in a feed stream that additionally contains a number of impurities (with respect to the factor VIII). One purpose of the present invention is to produce affinity ligands and preparations (such as chromatography media) comprising such ligands that allow rapid and highly specific purification of factor VIII from a particular feed stream. The factor VIII affinity ligands obtained herein may be tailored to the isolation of factor VIII from a particular feed stream, under specific preselected conditions. If an alternate production method for the factor VIII is used, producing a different feed stream, a different set of affinity ligands may be necessary to achieve the same level of purification. The new set of ligands can be readily obtained following the procedures outlined herein.

Factor VIII binding molecules of the invention bind factor VIII with high affinity, comparable to or superior to other proteins such as antibodies known to bind factor VIII. Further, preferred affinity ligands described herein release the factor VIII intact and in active form under specific release conditions.

Selecting Binding and Release Conditions

Polypeptide binding molecules according to the present invention were isolated using phage display technology, in a manner to identify factor VIII binding peptides exhibiting particular preselected properties of binding and release. According to this methodology, two solution conditions may be preselected, i.e., binding conditions and release conditions. The binding conditions are a set of solution conditions under which it is desired that a discovered binding polypeptide will bind the target factor VIII (or factor VIII-like polypeptide); the release conditions are a set of solution conditions under which it is desired that a discovered binding polypeptide will not bind the factor VIII (i.e., will dissociate from factor VIII). The two conditions may be selected to satisfy any criterion of the practitioner, such as ease of attaining the conditions, compatibility with other purification steps, lowered cost of switching between conditions compared to other affinity media, etc. Preferably, the two solution conditions are selected so as not to adversely affect the stability or activity of the target protein (factor VIII or factor VIII-like polypeptide) and so as to differ significantly with respect to at least one solution parameter. For example, in conducting the screening for suitable binding peptides described herein, binders were selected that dissociated from the target in the presence of an ethylene glycol-containing buffer, or conditions of lowered pH (i.e., pH 2), or combinations of those conditions, which differed from the conditions employed for binding. Another parameter that could be advantageously varied is the concentration of a salt, for example NaCl, in the binding and elution buffers.

Selection of a Parental Binding Domain

In conjunction with selecting specific solution conditions for the desired binding and release of the factor VIII, a parental binding domain is selected to serve as a structural template for the engineered binding molecules that will exhibit the desired binding and release capabilities. The binding domain may be a naturally occurring or synthetic protein, or a region or domain of a protein. The parental binding domain may be selected based on knowledge of a known interaction between the parental binding domain and the factor VIII, but this is not critical. In fact, it is not essential that the parental binding domain have any affinity for factor VIII at all: Its purpose is to provide a structure from which a multiplicity of analogues (a "library") can be generated, which multiplicity of analogues will include one or more analogues that exhibit the desired binding and release properties (and any other properties selected for). The binding conditions and the release conditions discussed supra may be selected with knowledge of the exact polypeptide that will serve as the parental binding domain, or with knowledge of a class of proteins or domains to which the parental binding domain belongs, or completely independently of the choice of the parental binding domain. Similarly, the binding and/or release conditions may be selected with regard to known interactions between a binding domain and the factor VIII, e.g., to favor the interaction under one or both of the solution conditions, or they may be selected without regard to such known interactions. Likewise, the parental binding domain can be selected taking into account the binding and/or release conditions or not, although it must be recognized that if the binding domain analogues are unstable under the binding or release conditions, no useful binding molecules may be obtained.

The nature of the parental binding domain greatly influences the properties of the derived peptides (analogues) that will be tested against the factor VIII molecule. In selecting the parental binding domain, the most important consideration is how the analogue domains will be presented to the factor VIII, i.e., in what conformation the factor VIII and the analogues will come into contact. In preferred embodiments, for example, the analogues will be generated by insertion of synthetic DNA encoding the analogue into a replicable genetic package, resulting in display of the domain on the surface of a microorganism, such as M13 phage, using techniques as described, e.g., in Kay et al., *Phage Display of Peptides and Proteins: A Laboratory Manual,* (Academic Press, Inc.; San Diego 1996) and U.S. Pat. No. 5,223,409 (Ladner et al.), incorporated herein by reference.

For formation of phage display libraries, it is preferred to use structured polypeptides as the binding domain template, as opposed to unstructured, linear peptides. Mutation of surface residues in a protein will usually have little effect on the overall structure or general properties (such as size, stability, and temperature of denaturation) of the protein; while at the same time mutation of surface residues may profoundly affect the binding properties of the protein. The more tightly a peptide segment is constrained, the less likely it is to bind to any particular target. If it does bind, however, the binding is likely to be tighter and more specific. Thus, it is preferred to select a parental binding domain and, in turn, a structure for the polypeptide analogues, that is constrained within a framework having some degree of rigidity.

Preferably the protein domain that is used as the template or parental domain for generating the library of domain analogues will be a small protein or polypeptide. Small proteins or polypeptides offer several advantages over large proteins: First, the mass per binding site is reduced. Highly stable protein domains having low molecular weights, e.g., Kunitz domains (~7 kDa), Kazal domains (~7 kDa), *Cucurbida maxima* trypsin inhibitor (CMTI) domains (~3.5 kDa), and endothelin (~2 kDa), can show much higher binding per gram than do antibodies (150 kDa) or single-chain antibodies (30 kDa). Second, the possibility of non-specific binding is reduced because there is less surface available. Third, small proteins or polypeptides can be engineered to have unique tethering sites in a way that is impracticable for larger proteins or antibodies. For example, small proteins can be engineered to have lysines only at sites suitable for tethering (e.g., to a chromatography matrix), but this is not feasible for antibodies. Fourth, a constrained polypeptide structure is more likely to retain its functionality when transferred with the structural domain intact from one framework to another. For instance, the binding domain structure is likely to be transferable from the framework used for presentation in a library (e.g., displayed on a phage) to an isolated protein removed from the presentation framework or immobilized on a chromatographic substrate.

Immobilization of the polypeptides according to the invention is contemplated, e.g., onto chromatographic matrices to form efficient factor VIII separation media for solutions such as whole blood or conditioned culture media containing factor VIII secreted from a transformant host cell. By selecting appropriate binding domain templates, binding polypeptides having a single free (unpaired with another cysteine that ordinarily forms a disulfide link) cysteine can be isolated. Such thiol-functional polypeptides can be used for highly stable immobilization to substrates by formation of a thioether with iodoacetamide, iodoacetic acid, or similar α-iodo carboxylic acid groups.

Similarly, the C-terminal carboxyl group of the polypeptide domain may be converted to a hydrazide (—NH—$NH_2$), for reaction with an aldehyde-functional substrate or other amine-reactive substrate. This technique is preferred.

There are many small, stable protein domains suitable for use as parental binding domains and for which the following useful information is available: (1) amino acid sequence, (2) sequences of several homologous domains, (3) 3-dimensional structure, and/or (4) stability data over a range of pH, temperature, salinity, organic solvent, oxidant concentration. Some examples are: Kunitz domains (58 amino acids, 3 disulfide bonds), Cucurbida maxima trypsin inhibitor domains (31 amino acids, 3 disulfide bonds), domains related to guanylin (14 amino acids, 2 disulfide bonds), domains related to heat-stable enterotoxin IA from gram negative bacteria (18 amino acids, 3 disulfide bonds), EGF domains (50 amino acids, 3 disulfide bonds), kringle domains (60 amino acids, 3 disulfide bonds), fungal carbohydrate-binding domains (35 amino acids, 2 disulfide bonds), endothelin domains (18 amino acids, 2 disulfide bonds), and Streptococcal G IgG-binding domain (35 amino acids, no disulfide bonds). Most but not all of these contain disulfide bonds that maintain and stabilize the structure. The parental binding domain may also be based on a single loop (one disulfide) of a microprotein that is homologous to a known protein domain or not. For example, constrained loops of 7 to 9 amino acids were used to form libraries for isolating factor VIII and factor VIII-like polypeptide binding molecules, as described below. Libraries based on these domains, preferably displayed on phage, can be readily constructed and used for the selection of binding molecules according to this invention.

Providing a Library of Parental Binding Domain Analogues

Once a parental binding domain has been selected, a library of potential binding molecules is created for screening against a target, in this case factor VIII and/or factor VIII-like proteins, under the desired binding conditions and (optionally) the desired elution (release) conditions. The library is created by making a series of analogues, each analogue corresponding to the parental binding domain except having one or more amino acid substitutions in the amino acid sequence of the domain. The amino acid substitutions are expected to alter the binding properties of the domain without significantly altering its structure, at least for most substitutions. It is preferred that the amino acid positions that are selected for variation (variable amino acid positions) will be surface amino acid positions, that is, positions in the amino acid sequence of the domains which, when the domain is in its most stable conformation, appear on the outer surface of the domain (i.e., the surface exposed to solution). Most preferably the amino acid positions to be varied will be adjacent or close together, so as to maximize the effect of substitutions. In addition, extra amino acids can be added into the structure of the parental binding domain. In preferred embodiments, especially where a great deal of information is available concerning the interactions of factor VIII with other molecules, particularly the parental binding domain, those amino acid positions that are essential to binding interactions will be determined and conserved in the process of building the analogue library (i.e., the amino acids essential for binding will not be varied).

The object of creating the analogue library is to provide a very large number of potential binding molecules for reaction with the factor VIII molecule, and in general the greater the number of analogues in the library, the greater the likelihood that at least one member of the library will bind to the factor VIII and release under preselected or desirable conditions for release. Designed libraries following a particular template structure and limiting amino acid variegation at particular positions are much preferred, since a single library can encompass all the designed analogues and the included sequences will be known and presented in roughly equal numbers. By contrast, random substitution at only six positions in an amino acid sequence provides over 60 million analogues, which is a library size that begins to present practical limitations even when utilizing screening techniques as powerful as phage display. Libraries larger than this would pose problems in handling, e.g., fermentation vessels would need to be of extraordinary size, and more importantly, the likelihood of having all of the planned polypeptide sequence variations represented in the prepared library would decrease sharply. It is therefore preferred to create a designed or biased library, in which the amino acid positions designated for variation are considered so as to maximize the effect of substitution on the binding characteristics of the analogue, and the amino acid residues allowed or planned for use in substitutions are limited, e.g., on the basis that they are likely to cause the analogue to bind under the solution conditions at which the library will be screened for binders.

As indicated previously, the techniques discussed in Kay et al., supra, and Ladner et al., U.S. Pat. No. 5,223,409 are particularly useful in preparing a library of analogues corresponding to a selected parental binding domain, which analogues will be presented in a form suitable for large-scale screening of large numbers of analogues with respect to a target factor VIII molecule. The use of replicable genetic packages, and most preferably bacteriophage, is a powerful method of generating novel polypeptide binding entities that involves introducing a novel, exogenous DNA segment into the genome of a bacteriophage (or other amplifiable genetic package) so that the polypeptide encoded by the non-native DNA appears on the surface of the phage. When the inserted DNA contains sequence diversity, then each recipient phage displays one variant of the template (parental) amino acid sequence encoded by the DNA, and the phage population (library) displays a vast number of different but related amino acid sequences.

In a screening procedure to obtain factor VIII binders according to this invention, a phage library is contacted with and allowed to bind a target factor VIII molecule, usually immobilized on a solid support. Non-binders are separated from binders. In various ways, the bound phage are liberated from the factor VIII, collected and amplified. Since the phage can be amplified through infection of bacterial cells, even a few binding phage are sufficient to reveal the gene sequence that encodes a binding entity. Using these techniques it is possible to recover a binding phage that is about 1 in 20 million in the population. One or more libraries, displaying 10–20 million or more potential binding polypeptides each, can be rapidly screened to find high-affinity factor VIII binders. When the selection process works, the diversity of the population falls with each round until only good binders remain, i.e., the process converges. Typically, a phage display library will contain several closely related binders (10 to 50 binders out of 10 million). Indications of convergence include increased binding (measured by phage titers) and recovery of closely related sequences. After a first set of binding peptides is identified, the sequence information can be used to design other libraries biased for members having additional desired properties, e.g., discrimination between factor VIII and particular fragments or closely related impurities in a particular feed stream.

Such techniques make it possible not only to screen a large number of potential binding molecules but make it practical to repeat the binding/elution cycles and to build secondary, biased libraries for screening analog-displaying packages that meet initial criteria. Using these techniques, an analogue biased library may be screened to reveal members that bind tightly (i.e., with high affinity) under the screening conditions.

Synthesis of Polypeptide Analogues

Following the procedures outlined above, additional binding molecules for factor VIII and/or factor VIII-like polypeptides may be isolated from the phage display libraries described herein or other phage display libraries or collections of potential binding molecules (e.g., combinatorial libraries of organic compounds, random peptide libraries, etc.). Once isolated, the sequence of any individual binding peptide or the structure of any binding molecule can be analyzed, and the binder may be produced in any desired quantity using known methods. For example, the polypeptide binding molecules described herein, since their sequences are now known, may advantageously be produced by chemical synthesis followed by treatment under oxidizing conditions appropriate to obtain the native conformation, i.e., the correct disulfide bond linkages. Synthesis may be carried out by methodologies well known to those skilled in the art (see, Kelley et al. in *Genetic Engineering Principles and Methods,* (Setlow, J. K., ed.), Plenum Press, NY., (1990) vol. 12, pp. 1–19; Stewart et al., *Solid-Phase Peptide Synthesis* (1989), W. H. Freeman Co., San Francisco). The binding molecules of the present invention can be made either by chemical synthesis or by semisynthesis. The chemical synthesis or semisynthesis methods allow the possibility of non-natural amino acid residues to be incorporated.

Polypeptide binding molecules of the present invention are preferably prepared using solid phase peptide synthesis (Merrifield, *J Am. Chem. Soc.,* 85: 2149 (1963); Houghten, *Proc. Natl. Acad. Sci. USA,* 82: 5132 (1985)). Solid phase synthesis begins at the carboxy-terminus of the putative polypeptide by coupling a protected amino acid to a suitable resin, which reacts with the carboxy group of the C-terminal amino acid to form a bond that is readily cleaved later, such as a halomethyl resin, e.g., chloromethyl resin and bromomethyl resin, hydroxymethyl resin, aminomethyl resin, benzhydrylamine resin, or t-alkyloxycarbonyl-hydrazide resin. After removal of the α-amino protecting group with, for example, trifluoroacetic acid (TFA) in methylene chloride and neutralizing in, for example, TEA, the next cycle in the synthesis is ready to proceed. The remaining α-amino and, if necessary, side-chain-protected amino acids are then coupled sequentially in the desired order by condensation to obtain an intermediate compound connected to the resin. Alternatively, some amino acids may be coupled to one another forming an oligopeptide prior to addition of the oligopeptide to the growing solid phase polypeptide chain.

The condensation between two amino acids, or an amino acid and a peptide, or a peptide and a peptide can be carried out according to the usual condensation methods such as azide method, mixed acid anhydride method, DCC (dicyclohexylcarbodiimide) method, active ester method (p-nitrophenyl ester method, BOP [benzotriazole-1-yl-oxytris (dimethylamino) phosphonium hexafluorophosphate] method, N-hydroxysuccinic acid imido ester method), and Woodward reagent K method.

Common to chemical synthesis of peptides is the protection of the reactive side-chain groups of the various amino acid moieties with suitable protecting groups at that site until the group is ultimately removed after the chain has been completely assembled. Also common is the protection of the α-amino group on an amino acid or a fragment while that entity reacts at the carboxyl group followed by the selective removal of the α-amino-protecting group to allow subsequent reaction to take place at that location. Accordingly, it is common that, as a step in the synthesis, an intermediate compound is produced which includes each of the amino acid residues located in the desired sequence in the polypeptide chain with various of these residues having side-chain protecting groups. These protecting groups are then commonly removed substantially at the same time so as to produce the desired resultant product following purification.

The typical protective groups for protecting the α- and ε-amino side chain groups are exemplified by benzyloxycarbonyl (Z), isonicotinyloxycarbonyl (iNOC), O-chlorobenzyloxycarbonyl [Z(NO$_2$)], p-methoxybenzyloxycarbonyl [Z(OMe)], t-butoxycarbonyl (Boc), t-amyioxycarbonyl (Aoc), isobornyloxycarbonyl, adamatyloxycarbonyl, 2-(4-biphenyl)-2-propyloxycarbonyl (Bpoc), 9-fluorenylmethoxycarbonyl (Fmoc), methylsulfonyiethoxycarbonyl (Msc), trifluoroacetyl, phthalyl, formyl, 2-nitrophenylsulphenyl (NPS), diphenylphosphinothioyl (Ppt), dimethylophosphinothioyl (Mpt), and the like.

As protective groups for the carboxy group there can be exemplified, for example, benzyl ester (OBzl), cyclohexyl ester (Chx), 4-nitrobenzyl ester (ONb), t-butyl ester (Obut), 4-pyridylmethyl ester (OPic), and the like. It desirable that specific amino acids such as arginine, cysteine, and serine possessing a functional group other than amino and carboxyl groups are protected by a suitable protective group as occasion demands. For example, the guanidino group in arginine may be protected with nitro, p-toluenesulfonyl, benzyloxycarbonyl, adamantyloxycarbonyl, p-methoxybenzenesulfonyl, 4-methoxy-2,6-dimethylbenzenesulfonyl (Mds), 1,3,5-trimethylphenysulfonyl (Mts), and the like. The thiol group in cysteine may be protected with p-methoxybenzyl, triphenylmethyl, acetylaminomethyl ethylcarbamoyl, 4-methylbenzyl, 2,4,6-trimethy-benzyl (Tmb), etc., and the hydroxyl group in the serine can be protected with benzyl, t-butyl, acetyl, tetrahydropyranyl, etc.

After the desired amino acid sequence has been completed, the intermediate polypeptide is removed from the resin support by treatment with a reagent, such as liquid HF and one or more thio-containing scavengers, which not only cleaves the polypeptide from the resin, but also cleaves all the remaining side-chain protecting groups. Following HF cleavage, the protein sequence is washed with ether, transferred to a large volume of dilute acetic acid, and stirred at pH adjusted to about 8.0 with ammonium hydroxide. Upon pH adjustment, the polypeptide takes its desired conformational arrangement.

Polypeptides according to the invention may also be prepared commercially by companies providing polypeptide synthesis as a service (e.g., BACHEM Bioscience, Inc., King of Prussia, Pa.; Quality Controlled Biochemicals, Inc., Hopkinton, Mass.).

Use of the Binding Molecules in Detection or Purification

For detection of factor VIII and/or factor VIII-like polypeptides in a solution such as blood or conditioned media suspected of containing it, a binding molecule according to the invention can be detectably labeled, e.g., radiolabeled or enzymatically labeled, then contacted with the solution, and thereafter formation of a complex between the binding molecule and the factor VIII target can be detected. A phage binding molecule according to the invention, i.e., a recombinant phage displaying a factor VIII binder polypeptide on its surface, may form a complex with factor VIII and/or factor VIII-like polypeptides that is detectable as a sediment in a reaction tube, which can be detected visually after settling or centrifugation.

Alternatively, a sandwich-type assay may be used, wherein a factor VIII binding molecule is immobilized on a solid support such as a plastic tube or well, or a chromatographic matrix such as sepharose beads, then the solution suspected of containing the factor VIII target is contacted with the immobilized binding molecule, non-binding materials are washed away, and complexed factor VIII or factor VIII-like polypeptide is detected using a suitable detection reagent, such as a monoclonal antibody recognizing the factor VIII target, which reagent is detectable by some conventional means known in the art, including being detectably labeled, e.g., radiolabeled or labeled enzymatically, as with horseradish peroxidase, and the like.

The binding molecules according to this invention will be extremely useful for isolation of factor VIII and/or factor VIII-like polypeptides by affinity chromatography methods. Any conventional method of chromatography may be employed. Preferably, an affinity ligand of the invention will be immobilized on a solid support suitable, e.g., for packing a chromatography column. The immobilized affinity ligand can then be loaded or contacted with a feed stream under conditions favorable to formation of binding molecule/factor VIII (or factor VIII-like polypeptide) complexes. Non-binding materials can be washed away, then the factor VIII (or factor VIII-like polypeptide) can be eluted by introducing solution conditions favoring dissociation of the binding complex.

Alternatively, batch chromatography can be carried out by mixing a solution containing the factor VIII target and the binding molecule, then isolating complexes of the factor VIII target and the binding molecules. For this type of separation, many methods are known. For example, the binding molecule can be immobilized on a solid support, then separated from the feed stream along with the factor VIII target by filtration. Or the binding molecule may be modified with its own affinity tag, such as a polyHis tail, which can be used to bind the binder after complexes have formed using an immobilized metal affinity chromatography. Once separated, the factor VIII target can be released from the binding molecule under elution conditions and recovered in pure form.

It should be noted that although precise binding conditions were preselected in obtaining the factor VIII-binding polypeptides disclosed herein, subsequent use in affinity purification may reveal more optimal binding and release conditions under which the same isolated affinity ligand will operate. Thus, it is not critical that the binding molecule, after isolation according to this invention, be always employed only at the binding and release conditions that led to its separation from the library.

Isolation of factor VIII binding molecules in accordance with this invention will be further illustrated below. The specific parameters included in the following examples are intended to illustrate the practice of the invention, and they are not presented to in any way limit the scope of the invention.

EXAMPLE I

The Isolation of Binding Molecules for a Factor VIII-like Polypeptide

The techniques described above were employed to isolate high affinity binding molecules for ligands for recombinantly produced factor VIII-like polypeptide consisting of two segments of human factor VIII, i.e., amino acids 1–743 and 1638 through 2332 of human factor VIII, as described in U.S. Pat. No. 5,661,008 (Almstedt et al.), obtained under the commercial designation of REFACTO® from Genetics Institute, Inc. (Cambridge, Mass.). The REFACTO® target was provided at a concentration of about 530 $\mu$g/ml (7800 IU/ml) in 19.4 mM His, 300 mM NaCl, 3.4 mM $CaCl_2$ and 0.1% TWEEN 80 (polyoxyethylene sorbitan monooleate), pH 7.0.

Three libraries, designated TN7 ($5\times10^9$ amino acid sequence diversity), TN8 ($6\times10^9$ amino acid sequence diversity), and TN9 ($5\times10^9$ amino acid sequence diversity), were constructed for expression of diversified polypeptides on M13 phage. Each library was screened for binders to purified REFACTO®. Each of the libraries was constructed to display a microprotein based on an 11- or 12-amino acid template. The TN7 library utilized a template sequence of Xaa-Xaa-Cys-Xaa-Xaa-Xaa-Xaa-Xaa-Cys-Xaa-Xaa (SEQ ID NO: 33); the TN8 library utilized a template sequence of Xaa-Xaa-Cys-Xaa-Xaa-Xaa-Xaa-Xaa-Xaa-Cys-Xaa-Xaa (SEQ ID NO: 34); the TN9 library utilized a template sequence of Xaa-Cys-Xaa-Xaa-Xaa-Xaa-Xaa-Xaa-Xaa-Cys-Xaa (SEQ ID NO: 35).

Three rounds of screenings were carried out for each library. At the conclusion of the third round of screening eluted phage were propagated, and individual isolates from each library (96 per elution condition) were selected randomly and tested by standard ELISA techniques for binding to the factor VIII target. Bound phage were detected with HRP conjugated anti-M13 polyclonal antibody (Pharmacia). TMB Peroxidase substrate was used for HRP in the ELISA detection mechanism. TMB substrate produces a blue color after peroxidase digestion. The color is quantitated by absorbance at $OD_{630}$. Phage isolates that provided a significant signal ($OD_{630}$>0.25) above background were considered positive clones. DNA sequencing of these isolates was performed to identify the displayed peptide.

Amino acid sequences of the displayed peptides were deduced from the obtained DNA sequences. Sequence data from the phage isolates were grouped by library and sorted according to the degree of similarity. The frequency at which any given sequence was obtained was noted since this indicates selection for a specific binder. Phage isolates having the same display peptide were found to be present in phage populations obtained by both of the two elution methods.

TABLE 1

Amino acid sequences of target-binding polypeptides from the TN7 library

| TN7 isolate | sequence | frequency (elution) | ELISA signal | SEQ ID NO: |
|---|---|---|---|---|
| A06 | His-Ser-Cys-Gly-Ser-Trp-Leu-Phe-Pro-Cys-Phe-Ala | 7/96 (EG) | 0.5 | 4 |
| A08 | Phe-Gly-Cys-Ser-Trp-Leu-Phe-Pro-Cys-Pro-Phe | 2/96 (EG) | 0.4 | 5 |
| D03 | Pro-His-Cys-Asn-Trp-Leu-Phe-Pro-Cys-Ser-Leu | 7/192 (EG/pH2) | 0.2 | 6 |
| D04 | Arg-Leu-Cys-Ser-Trp-Ile-Ser-Pro-Cys-Ser-Ala | 6/192 (EG/pH2) | 0.3 | 7 |
| A09 | Phe-His-Cys-lle-Gly-Val-Trp-Phe-Cys-Leu-His | 2/192 (EG/pH2) | 0.1 | 8 |
| C5/G10 | Arg-Leu-Cys-Ser-Trp-Val-Ser-Pro-Cys-Ser-Ala | 1/96 (EG) | 0.5 | 9 |

TABLE 2

Amino acid sequences of target-binding polypeptides from the TN8 library

| TN8 isolate | sequence | frequency (elution) | ELISA signal | SEQ ID NO: |
|---|---|---|---|---|
| C10 | His-Pro-Cys-Gly-Ser-Trp-Leu-Arg-Pro-Cys-Leu-His | 10/192 (EG/pH2) | 1.0 | 10 |
| B05 | Arg-Gly-Cys-Gly-Ser-Trp-Leu-Arg-Pro-Cys-Leu-Asp | 2/192 (EG/pH2) | 0.2 | 11 |
| E04 | His-Pro-Cys-Gly-Ser-Trp-Leu-His-Pro-Cys-Ala-Ala | 3/192 (EG/PH2) | 0.3 | 12 |
| F02 | His-Pro-Cys-Gly-Ser-Trp-Phe-Asn-Pro-Cys-Ala-His | 5/192 (EG/pH2) | 0.3 | 13 |
| A02 | His-Pro-Cys-Gly-Ser-Trp-Phe-Arg-Pro-Cys-Phe-His | 3/96 (EG) | 0.7 | 14 |
| H07 | His-Ala-Cys-Gly-Ser-Trp-Phe-Arg-Pro-Cys-His-Ala | 3/192 | 0.4 | 15 |
| E02 | His-Leu-Cys-Gly-Ala-Trp-Phe-Arg-Pro-Cys-Asp-Ala | 6/192 (EG/pH2) | 0.4 | 16 |
| C12 | His-Leu-Cys-Phe-Ala-Trp-Phe-Arg-Pro-Cys-Asp-Ala | 1/96 (EG) | 0.4 | 17 |
| A01 | His-Gly-Cys-Gly-Ala-Trp-Phe-Arg-Pro-Cys-His-Ala | 4/192 (EG/pH2) | 0.2 | 18 |
| E01 | His-Pro-Cys-Gly-Ala-Trp-Phe-Asn-Pro-Cys-Pro-Arg | 1/96 (pH2) | 0.2 | 19 |
| H08 | His-Pro-Cys-Gly-Ala-Trp-Leu-Arg-Pro-Cys-Tyr-Asn | 1/96 (EG) | 1.0 | 20 |
| A11/G10 | His-Arg-Cys-Gly-Ser-Trp-Leu-His-Pro-Cys-Leu-Ala | 1/96 (EG) | 0.3 | 21 |

TABLE 3

Amino acid sequences of target-binding polypeptides from the TN9 library

| TN9 isolate | sequence (elution) | frequency signal | ELISA | SEQ ID NO: |
|---|---|---|---|---|
| B04 | Phe-Cys-Trp-Val-Phe-Ala-Phe-Asp-His-Cys-His | 6/192 (EG/pH2) | 0.8 | 22 |
| G02 | Phe-Cys-Trp-Val-His-Pro-Phe-Ala-His-Cys-Leu | 2/96 (EG) | 0.2 | 23 |
| B01 | Phe-Cys-His-Val-Phe-His-Phe-Ser-His-Cys-Asp | 5/192 (EG/pH2) | 0.2 | 24 |
| A01 | Phe-Cys-Trp-Val-Phe-Ala-Phe-Asp-His-Cys-His | 12/192 (EG/pH2) | 1.2 | 25 |
| E03 | Phe-Cys-Trp-Val-Phe-Asn-Phe-Ser-His-Cys-Ser | 4/192 (EG/pH2) | 1.1 | 26 |
| C02 | Phe-Cys-Trp-Val-Phe-Pro-Phe-Asn-His-Cys-Asp | 5196 (pH2) | 0.4 | 27 |
| E12 | Phe-Cys-Trp-Val-Phe-Pro-Phe-Asn-His-Cys-Ser | 6/96 (EG) | 1.0 | 28 |
| E09 | Phe-Cys-Trp-Val-Phe-Pro-Phe-Gln-His-Cys-Ala | 4/192 (EG/p112) | 1.1 | 29 |
| D06 | Phe-Cys-Trp-Val-Phe-Pro-Phe-His-His-Cys-Phe | 2/192 (EG/pH2) | 0.3 | 30 |
| C01 | Phe-Cys-His-Val-Phe-Asn-Phe-Val-His-Cys-Ser | 2/192 (EG/pH2) | 0.5 | 31 |
| H11 | Phe-Cys-His-Val-Phe-Pro-Phe-Leu-His-Cys-Asp | 2/192 (EG/pH2) | 0.2 | 32 |

Example II

Preparation of Affinity Ligands for a Factor VIII Target

Based on the data presented above, nine peptides were selected and synthesized for immobilization on an affinity matrix material. The peptides synthesized are set forth in Table 4.

The nine lead affinity peptides were produced by classical solid-phase synthetic methods as described above. To facilitate immobilization on a solid support, a short seven amino acid hydrazide-functional linker region (—PGPEGGGS—NHNH$_2$; SEQ ID NO: 45) was incorporated at the carboxy-terminus of seven of the peptides (see Table 4). An alterna-

TABLE 4

Amino Acid Sequence of Affinity Ligands and their Densities on Solid Support

| Affinity Ligand | Phage Isolate | Sequence (disulfide loop underlined) | Ligand Density mg/ml (μmol/ml) |
|---|---|---|---|
| CS-453 | C10-TN8 | AEGTGDHP<u>CGSWLRPC</u>LHDPGPEGGGS-NHNH$_2$ | 2.64 (0.98) |
| CS-454 | E02-TN8 | AEGTGDHL<u>CGAWFRPC</u>DADPGPEGGGS-NHNH$_2$ | 1.79 (0.67) |
| CS-455 | A09-TN7 | AEGTGDFH<u>CIGVWFC</u>LHDPGPEGGGS-NHNH$_2$ | 2.21 (0.83) |
| CS-456 | A08-TN7 | AEGTGDFG<u>CSWLFPCP</u>FDPGPEGGGS-NHNH$_2$ | 3.69 (1.43) |
| CS-458 | B04-TN9 | AEGTGDF<u>CWVFAFDHC</u>HDPGPEGGGS-NHNH$_2$ | 3.15 (1.17) |
| CS-459 | E09-TN9 | AEGTGDF<u>CWVFPFQHC</u>ADPGPEGGGS-NNNH$_2$ | 2.72 (1.02) |
| CS-460 | D06-TN9 | AEGTGDF<u>CWVFPFHHC</u>FDPGPEGGGS-NNNH$_2$ | 4.24 (1.54) |
| GI-1 | C05/G10-TN7 | Acetyl-AEGTGDRL<u>CSWVSPC</u>SADPEGGGSK | 0.83 (0.32) |
| GI-2 | A11/G10-TN8 | Acetyl-AEGTGDHR<u>CGSWLHPC</u>LADPEGGGSK | 0.43 (0.16) |

The affinity peptides of Table 4 are identified, in above order, with SEQIDNOs:36–44.

tive immobilization linker was used with two of the peptides (GI-1 and GI-2 in Table 4), i.e., —PEGGGSK; (SEQ ID NO: 46), exhibiting a C-terminal lysine for immobilization and an acetylated amino-terminus.

The candidate ligands were immobilized onto a formyl-substituted ethylene glycol-methacrylate chromatographic resin (Toyopearl Formyl 650-M, pore size of 1000 Å; TosoHaas, Montgomeryville, Pa.). The hydrazide-containing peptides were immobilized by facilitating hydrazone bond formation, the GI-1 and -2 peptides were immobilized via reductive amination using NaCNBH$_3$. The amount of polypeptide immobilized on the solid support was determined by quantifying the amount of free polypeptide remaining in solution. The amount of ligand immobilized per ml of resin was in the range of 0.7–1.5 μmol for the hydrazine-immobilized peptides.

The nine peptides were evaluated by affinity chromatography for their ability to capture the REFACTO® described in Example I, under specific binding and release conditions. The buffers used in these evaluations are set forth in Table 5.

TABLE 5

Binding and Elution Conditions Employed

| | |
|---|---|
| Binding Buffer | 100 mM NH$_4$OAc, pH 6.3, 0.8 M NaCl, 1 M Sorbitol, 0.02% Tween 80, 3 mM EDTA, 5 mM CaCl$_2$ |
| Elution Buffer A | 50% ethylene glycol, 20 mM His, 0.25 M NaCl, 20 mM CaCl$_2$, 0.01% Tween 80, pH 7 |
| Elution Buffer B | 0.35 M CaCl$_2$, 20 mM His, 0.3 M NaCl, 0.1% Tween 80, pH 7 |
| pH 2 Clean | 100 mM Gly, 1 M NaCl, pH 2 |

The factor VIII-like polypeptide (REFACTO®) was diluted in SP Buffer to a concentration of 150 μg/ml. The affinity resins (~350 μl) were each packed into glass columns, and approximately 150 μg of the factor VIII target was applied to the prepared affinity columns at a flow rate of 200 μl/minute (linear velocity of 170 cm/hour). The bound material was eluted sequentially with the buffers as shown in Table 5, and protein elution was monitored by UV absorbance at 280 nm. Fractions were collected and the mass and activity of recovered factor VIII-like polypeptide was determined by reversed-phase HPLC and by enzymatic assay.

For the mass determination, a standard curve with REFACTO® (0–200 μg) was generated and the amount present in each fraction was calculated according to techniques well known in the art. Reversed-phase HPLC in the presence of 20 mM EDTA was used to disrupt the REFACTO® molecule into its component subunits, which were eluted with a gradient of acetonitrile/0.01% TFA. The activity assay was a Factor IX-, X-based assay. The results for each affinity resin are set forth below (Table 6).

TABLE 6

Summary of Data Obtained with Nine Affinity Ligands

| Peptide | Assay | Elution Condition (% recovery) | | | | Total |
|---|---|---|---|---|---|---|
| | | Flow | A | B | pH2 | |
| Untreated Resin | RP-HPLC | 64.4 | 2.8 | 0 | 0 | 67.2 |
| | Activity | 64.4 | 0.6 | | | 65.0 |

TABLE 6-continued

Summary of Data Obtained with Nine Affinity Ligands

| Peptide | Assay | Elution Condition (% recovery) | | | | Total |
|---|---|---|---|---|---|---|
| | | Flow | A | B | pH2 | |
| CS-453 | RP-HPLC | 0 | 43.2 | 0 | 0 | 43.2 |
| | Activity | 0 | 26.4 | | | 26.4 |
| CS-454 | RP-HPLC | 2.5 | 45.1 | 0 | 0 | 47.6 |
| | Activity | 2.2 | 42.4 | | | 44.6 |
| CS-455 | RP-HPLC | 65.8 | 1.4 | 0 | 0 | 67.2 |
| | Activity | 61.6 | 1.3 | | | 62.9 |
| CS-456 | RP-HPLC | 3.4 | 44.8 | 0 | 0 | 48.2 |
| | Activity | 4.8 | 43.0 | | | 47.8 |
| CS-458 | RP-HPLC | 1.8 | 54.3 | 0 | 0 | 56.1 |
| | Activity | 1.4 | 55.6 | | | 57.0 |
| CS-459 | RP-HPLC | 1.6 | 42.1 | 0 | 0 | 43.7 |
| | Activity | 6.4 | 31.2 | | | 37.6 |
| CS-460 | RP-HPLC | 24.6 | 28.8 | 0 | 0 | 53.4 |
| | Activity | 28.4 | 0 | | | 28.4 |
| GI-1 | RP-HPLC | 65.7 | 0 | 0 | 0 | 65.7 |
| | Activity | 64.0 | 0 | | | 64.0 |
| GI-2 | RP-HPLC | 31.3 | 28.1 | 0 | 2.0 | 61.4 |
| | Activity | 33.7 | 20.3 | | | 53.9 |

In general, the total amount of the factor VIII target recovered after chromatography over the nine ligands was in the range of 40–67%. The polypeptide ligands CS-453, CS-454, CS-456, and CS-459 captured virtually all of the factor VIII target applied, with bound material being eluted in the presence of ethylene glycol. No activity was found in the pH 2 eluant, therefore it was assumed that none of the target remained bound to the ligand. The inability of the CS-455 and GI-1 resins to capture the target may be due to degradation or instability of the peptide, or to low ligand density on the support.

Example III

Comparative Binding of nhfVIII and REFACTO®

Experiments were conducted to demonstrate that the immobilized polypeptide ligands of Example II bind and release native human factor VIII (nhfVIII) under similar conditions and with similar yields as observed with the factor VIII-like polypeptide REFACTO®.

For these experiments, nhfVIII was obtained from American Diagnostica, Inc. (Greenwich, Conn.; product #408 nat) in the form of a lyophilized powder containing stabilizing agents. The nhfVIII was reconstituted according to the manufacturer's instructions in a reconstituting buffer (72 mM NH$_4$OAc, pH 6.3, 360 mM NaCl, 0.04% TWEEN 80 (Buffer 1).

A commercial ELISA kit (IMUBIND fVIII ELISA kit, Product #884, American, Inc., Greenwich, Conn.) developed to detect factor VIII was used according to the manufacturer's specifications in order to detect both the REFACTO® and the nhfVIII targets. The kit employs a sandwich ELISA assay in which the target is captured by an immobilized monoclonal antibody and the captured target is detected with a second monoclonal antibody-horseradish peroxidase (HRP) conjugate. Addition of the peroxidase substrate and its subsequent reaction with the HRP produces a blue color (detected at 630 nm) which changes to yellow (detected at 450 nm) on addition of the 0.5N sulfuric acid stop solution. Color response is calibrated with factor VIII standards provided by the manufacturer.

REFACTO® binding was tested in Buffer 1. The binding of both REFACTO® and nfhVIII were tested using three affinity resins prepared as in Example II, using the affinity peptides CS-454, CS-456, and CS-458 immobilized on Toyopearl Formyl 650-M medium. Ligand density for each polypeptide was 1.79 mg/ml (0.67 µmol/ml), 3.69 mg/ml (1.43 µmol/ml) and 3.15 mg/ml (1.17 µmol/ml) respectively.

For each of the three immobilized peptides tested, peptide-beads from 200 ml of a 50% slurry of Toyopearl-coupled polypeptide suspension were centrifuged briefly (30 seconds at 2000 x g at room temperature), the supernatant fluid was removed, and the beads (pellets) were washed two times. For each wash, the beads were resuspended in 500 µl of Buffer 1 and centrifuged as before.

The stock solution of REFACTO® was diluted to a final concentration of 200 U/ml in Buffer 1 and 250 µl of the diluted solution (~50 U total) was added to a washed pellet of each of the peptide-beads. The suspension was incubated on an end-over-end mixer at RT for one hour, after which binding period the beads were pelleted by centrifugation (30 seconds, 2000 x g) and the supernatant solutions, representing the unbound fraction ("Unbound" in Table 7, below), were removed and retained for assay of unbound factor VIII activity.

The pelleted beads were washed one time by adding 250 µl of Buffer 1, mixed briefly and the suspension centrifuged as before. The supernatant solutions ("Wash" in Table 7) were removed and retained for assay of factor VIII activity.

The washed pellets were resuspended in 250 µl of Buffer A (20 mM L-Histidine-HCl, 250 mM NaCl, 20 mM $CaCl_2$, 0.01% TWEEN 80, 50% ethylene glycol, pH 6.3) and incubated on an end-over-end mixer for 15 minutes at room temperature. At the end of the elution period, the suspensions were centrifuged as above. The supernatant solutions ("Eluate" in Table 7) were removed and retained for assay of eluted factor VIII activity.

The starting (diluted) REFACTO® solution (Input) and each sample (Unbound, Wash, and Eluate) taken as described above were diluted 1:1400 in Assay Diluent (provided with kit), then subjected to ELISA using the commercial factor VIII assay kit. Table 7 summarizes the results.

TABLE 7

Batch Binding and Elution of REFACTO ® with Immobilized Polypeptide Ligands

| Immobilized | % of Input Recovered in: | | | | |
| --- | --- | --- | --- | --- | --- |
| Peptide Ligand | Input | Unbound | Wash | Eluate | Total |
| CS-454 | 100 | 24 | 12 | 49 | 85 |
| CS-456 | 100 | 47 | 20 | 24 | 91 |
| CS-458 | 100 | 20 | 10 | 47 | 76 |

For each immobilized polypeptide tested, nearly all of the REFACTO® (>75%) added to the binding reaction was recovered in the Unbound, Wash, and Eluate fractions. A small amount of material (10%–25%) may have been retained on the beads following elution.

Next the affinity beads were regenerated by one wash in 50% ethylene glycol, 20 mM His, 0.25M NaCl, 20 mM $CaCl_2$, 0.01% TWEEN 80, pH 7, and two washes with 250 µl of 30 mM $H_3PO_4$, 1M NaCl, pH 2 (15 minutes for each wash). Following the pH 2 washes, the beads were washed once in PBS containing 0.05% azide and stored at 4° C.

A sample of nhfVIII was diluted to a final concentration of 100 U/ml by addition of 2.32 ml $H_2O$, 180 µl 1M $NH_4OAc$, pH 6.3 (to 72 mM), and 1 µl TWEEN 80 (to 0.04%). REFACTO® stock solution was diluted to 100 U/ml in a modified Buffer 1, in which the NaCl concentration was reduced from 660 mM to 330 mM.

Immobilized peptides were tested for binding to nhFVIII in comparison with REFACTO®. As a non-binding control, a polypeptide from the TN9 library (B10), which binds to an unrelated target and does not bind to a factor VIII target, was immobilized on the same methacrylate beads, as described above. Next, nhfVIII and REFACTO(® solutions were mixed with regenerated affinity beads bearing the CS-454, CS-456, and CS-458 ligands in a comparative batch purification procedure. The reaction conditions are set forth in Table 8.

TABLE 8

Reaction Conditions for nhfVIII Binding Test

| Immobilized Peptide Ligand | Volume Bead Slurry (µl) | Target (100 U/ml) | Reaction Volume (µl) |
| --- | --- | --- | --- |
| CS-454 | 200 | hfVIII | 500 |
| CS-456 | 200 | hfVIII | 500 |
| CS-458 | 200 | hfVIII | 500 |
| TN9-B10 | 200 | hfVIII | 500 |
| CS-458 | 100 | REFACTO ® | 250 |
| TN9-B10 | 100 | REFACTO ® | 250 |

The results of these trials are set forth in Table 9.

TABLE 9

Batch Binding and Elution of nhfVIII and REFACTO ® with Immobilized Polypeptide Ligands

| Immobilized Peptide Ligand | Target | % of Total Recovered in: | | |
| --- | --- | --- | --- | --- |
| | | Unbound | Wash | Eluate |
| CS-454 | nhfVIII | 67 | 12 | 21 |
| CS-456 | nhfVIII | 70 | 14 | 16 |
| CS-458 | nhfVIII | 48 | 13 | 39 |
| TN9-B10 | nhfVIII | 86 | 14 | 0 |
| CS-458 | REFACTO ® | 59 | 14 | 27 |
| TN9-B10 | REFACTO ® | 90 | 10 | 0 |

In conclusion, the immobilized polypeptide ligands, CS-458, CS-454, and CS-456 bind and release nhfVIII under similar conditions and with similar yields as observed previously with a factor VIII-like polypeptide.

Following the foregoing description, the characteristics important for affinity binding molecules permitting detection or separation of factor VIII or factor VIII-like polypeptides in or from any solution can be appreciated. Additional binding molecule embodiments of the invention and alternative methods adapted to a particular solution or feed stream will be evident from studying the foregoing description. All such embodiments and obvious alternatives are intended to be within the scope of this invention, as defined by the claims that follow.

Each of the publications referred to above is hereby incorporated by reference.

What is claimed is:

1. A polypeptide which binds factor VIII or a fragment of factor VIII, wherein said fragment retains the procoagulant properties of factor VIII, wherein said polypeptide comprises the amino acid sequence:

$X_{10}$-$X_{11}$-Cys-$X_{12}$-$X_{13}$-Trp-$X_{14}$-$X_{15}$-Pro-Cys-$X_{16}$-$X_{17}$ (SEQ ID NO: 2), wherein $X_{10}$ is Arg or His; $X_{11}$ is Ala, Arg, Gly, Leu or Pro; $X_{12}$ is Gly or Phe; $X_{13}$ is Ala or Ser; $X_{14}$ is Leu or Phe; $X_{15}$ is Arg, Asn or His; $X_{16}$ is Ala, Asp, His, Leu, Phe, Pro, or Tyr; $X_{17}$ is Ala, Arg, Asn, Asp, or His.

2. A polypeptide which binds factor VIII or a fragment of factor VIII, wherein said fragment retains the procoagulant properties of factor VIII, wherein said polypeptide comprises the amino acid sequence selected from the group consisting of:

His-Pro-Cys-Gly-Ser-Trp-Leu-Arg-Pro-Cys-Leu-His (SEQ ID NO: 10);
Arg-Gly-Cys-Gly-Ser-Trp-Leu-Arg-Pro-Cys-Leu-Asp (SEQ ID NO: 11);
His-Pro-Cys-Gly-Ser-Trp-Leu-His-Pro-Cys-Ala-Ala (SEQ ID NO: 12);
His-Pro-Cys-Gly-Ser-Trp-Phe-Asn-Pro-Cys-Ala-His (SEQ ID NO: 13);
His-Pro-Cys-Gly-Ser-Trp-Phe-Arg-Pro-Cys-Phe-His (SEQ ID NO: 14);
His-Ala-Cys-Gly-Ser-Trp-Phe-Arg-Pro-Cys-His-Ala (SEQ ID NO: 15);
His-Leu-Cys-Gly-Ala-Trp-Phe-Arg-Pro-Cys-Asp-Ala (SEQ ID NO: 16);
His-Leu-Cys-Phe-Ala-Trp-Phe-Arg-Pro-Cys-Asp-Ala (SEQ ID NO: 17);
His-Gly-Cys-Gly-Ala-Trp-Phe-Arg-Pro-Cys-His-Ala (SEQ ID NO: 18);
His-Pro-Cys-Gly-Ala-Trp-Phe-Asn-Pro-Cys-Pro-Arg (SEQ ID NO: 19);
His-Pro-Cys-Gly-Ala-Trp-Leu-Arg-Pro-Cys-Tyr-Asn (SEQ ID NO:20); and
His-Arg-Cys-Gly-Ser-Trp-Leu-His-Pro-Cys-Leu-Ala (SEQ ID NO:21).

3. A polypeptide according to claim 2, consisting of an amino acid sequence selected from the group consisting of:

AEGTGDHPCGSWLRPCLHDPGPEGGGS-NHNH$_2$ (SEQ ID NO:36);
AEGTGDHLCGAWFRPCDADPGPEGGGS-NHNH$_2$ (SEQ ID NO:37); and
Acetyl-AEGTGDHRCGSWLHPCLADPGEGGGSK (SEQ ID NO:44).

4. The polypeptide of claim 1 which is capable of binding to human factor VIII, or a fragment of human factor VIII wherein said fragment retains the procoagulant properties of factor VIII, when in a solution comprising: 100 mM NH$_4$OAc, 0.8M NaCl, 1M Sorbitol, 0.02% polyoxyethylene sorbitan monooleate, 3 mM EDTA, 5 mM CaCl$_2$, pH 6.3 and dissociating from human factor VIII or said fragment of human factor VIII, when in a solution containing 50% ethylene glycol.

5. The polypeptide according to claim 4, which dissociates from human factor VIII or a fragment of human factor VIII, wherein said fragment retains the procoagulant properties of human factor VIII, when contacted with a solution comprising 50% ethylene glycol, 20 mM His, 0.25M NaCl, 20 mM CaCl$_2$, and 0.01% polyoxyethylene sorbitan monooleate, pH 7.

6. The polypeptide according to claim 4, wherein the polypeptide comprises an amino acid sequence selected from the group consisting of:

His-Pro-Cys-Gly-Ser-Trp-Leu-Arg-Pro-Cys-Leu-His (SEQ ID NO: 10);
Arg-Gly-Cys-Gly-Ser-Trp-Leu-Arg-Pro-Cys-Leu-Asp (SEQ ID NO: 1);
His-Pro-Cys-Gly-Ser-Trp-Leu-His-Pro-Cys-Ala-Ala (SEQ ID NO: 12);
His-Pro-Cys-Gly-Ser-Trp-Phe-Asn-Pro-Cys-Ala-His (SEQ ID NO: 13);
His-Pro-Cys-Gly-Ser-Trp-Phe-Arg-Pro-Cys-Phe-His (SEQ ID NO: 14);
His-Ala-Cys-Gly-Ser-Trp-Phe-Arg-Pro-Cys-His-Ala (SEQ ID NO: 15);
His-Leu-Cys-Gly-Ala-Trp-Phe-Arg-Pro-Cys-Asp-Ala (SEQ ID NO: 16);
His-Leu-Cys-Phe-Ala-Trp-Phe-Arg-Pro-Cys-Asp-Ala (SEQ ID NO: 17);

His-Gly-Cys-Gly-Ala-Trp-Phe-Arg-Pro-Cys-His-Ala (SEQ ID NO: 18);

His-Pro-Cys-Gly-Ala-Trp-Phe-Asn-Pro-Cys-Pro-Arg (SEQ ID NO: 19);

His-Pro-Cys-Gly-Ala-Trp-Leu-Arg-Pro-Cys-Tyr-Asn (SEQ ID NO:20); and

His-Arg-Cys-Gly-Ser-Trp-Leu-His-Pro-Cys-Leu-Ala (SEQ ID NO:21).

7. The polypeptide according to claim 6, wherein the polypeptide consists of an amino acid sequence selected from the group consisting of:

AEGTGDHPCGSWLRPCLHDPGPEGGGS-NHNH$_2$ (SEQ ID NO:36);

AEGTGDHLCGAWFRPCDADPGPEGGGS-NHNH$_2$ (SEQ ID NO:37); and

Acetyl-AEGTGDHRCGSWLHPCLADPGEGGGSK (SEQ ID NO:44).

8. A method for detecting human factor VIII or a fragment of human factor VIII, wherein said fragment retains the procoagulant properties of human factor VIII, in a solution comprising:

(a) contacting said solution with a polypeptide of claim 1, and (b) determining whether binding has occurred between said polypeptide and said factor VIII or said fragment of factor VIII.

9. A method for purifying human factor VIII or a fragment of human factor VIII, wherein said fragment retains the procoagulant properties of human factor VIII, comprising:

(a) immobilizing a polypeptide of claim 1 on a solid support, and (b) contacting a solution containing said human factor VIII or said fragment of human factor VIII with the immobilized polypeptide on a solid support, and (c) purifying said human factor VIII or said fragment of human factor VIII by separating the solution from said solid support.

10. A method according to claim 8 or claim 9, wherein said polypeptide comprises an amino acid sequence selected from the group consisting of:

His-Pro-Cys-Gly-Ser-Trp-Leu-Arg-Pro-Cys-Leu-His (SEQ ID NO: 10);

Arg-Gly-Cys-Gly-Ser-Trp-Leu-Arg-Pro-Cys-Leu-Asp (SEQ ID NO: 1);

His-Pro-Cys-Gly-Ser-Trp-Leu-His-Pro-Cys-Ala-Ala (SEQ ID NO: 12);

His-Pro-Cys-Gly-Ser-Trp-Phe-Asn-Pro-Cys-Ala-His (SEQ ID NO: 13);

His-Pro-Cys-Gly-Ser-Trp-Phe-Arg-Pro-Cys-Phe-His (SEQ ID NO: 14);

His-Ala-Cys-Gly-Ser-Trp-Phe-Arg-Pro-Cys-His-Ala (SEQ ID NO: 15);

His-Leu-Cys-Gly-Ala-Trp-Phe-Arg-Pro-Cys-Asp-Ala (SEQ ID NO: 16);

His-Leu-Cys-Phe-Ala-Trp-Phe-Arg-Pro-Cys-Asp-Ala (SEQ ID NO: 17);

His-Gly-Cys-Gly-Ala-Trp-Phe-Arg-Pro-Cys-His-Ala (SEQ ID NO: 18);

His-Pro-Cys-Gly-Ala-Trp-Phe-Asn-Pro-Cys-Pro-Arg (SEQ ID NO:19);

His-Pro-Cys-Gly-Ala-Trp-Leu-Arg-Pro-Cys-Tyr-Asn (SEQ ID NO:20); and

His-Arg-Cys-Gly-Ser-Trp-Leu-His-Pro-Cys-Leu-Ala (SEQ ID NO:2 1).

11. A method according to claim 10 wherein said polypeptide consists of an amino acid sequence selected from the group consisting of:

AEGTGDHPCGSWLRPCLHDPGPEGGGS-NHNH$_2$ (SEQ ID NO:36);

AEGTGDHLCGAWFRPCDADPGPEGGGS-NHNH$_2$ (SEQ ID NO:37); and

Acetyl-AEGTGDHRCGSWLHPCLADPGEGGGSK (SEQ ID NO:44).

12. A separation media comprising:

(a) a chromatographic matrix material, and, immobilized thereon, (b) a polypeptide comprising the amino acid sequence: $X_{10}$-$X_{11}$-Cys-$X_{12}$-$X_{13}$-Trp-$X_{14}$-$X_{15}$-Pro-Cys-$X_{16}$-$X_{17}$ (SEQ ID NO: 2), wherein $X_{10}$ is Arg or His; $X_{11}$ is Ala, Arg, Gly, Leu or Pro; $X_{12}$ is Gly or Phe; $X_{13}$ is Ala or Ser; $X_{14}$ is Leu or Phe; $X_{15}$ is Arg, Asn or His; $X_{16}$ is Ala, Asp, His, Leu, Phe, Pro, or Tyr; $X_{17}$ is Ala, Arg, Asn, Asp, or His.

13. The separation media according to claim 12 wherein said polypeptide is selected from the group consisting of:

His-Pro-Cys-Gly-Ser-Trp-Leu-Arg-Pro-Cys-Leu-His (SEQ ID NO: 10);

Arg-Gly-Cys-Gly-Ser-Trp-Leu-Arg-Pro-Cys-Leu-Asp (SEQ ID NO: 1);

His-Pro-Cys-Gly-Ser-Trp-Leu-His-Pro-Cys-Ala-Ala (SEQ ID NO: 12);

His-Pro-Cys-Gly-Ser-Trp-Phe-Asn-Pro-Cys-Ala-His (SEQ ID NO: 13);

His-Pro-Cys-Gly-Ser-Trp-Phe-Arg-Pro-Cys-Phe-His (SEQ ID NO: 14):

His-Ala-Cys-Gly-Ser-Trp-Phe-Arg-Pro-Cys-His-Ala (SEQ ID NO: 15);

His-Leu-Cys-Gly-Ala-Trp-Phe-Arg-Pro-Cys-Asp-Ala (SEQ ID NO: 16);

His-Leu-Cys-Phe-Ala-Trp-Phe-Arg-Pro-Cys-Asp-Ala (SEQ ID NO: 17);

His-Gly-Cys-Gly-Ala-Trp-Phe-Arg-Pro-Cys-His-Ala (SEQ ID NO: 18);

His-Pro-Cys-Gly-Ala-Trp-Phe-Asn-Pro-Cys-Pro-Arg (SEQ ID NO:19);

His-Pro-Cys-Gly-Ala-Trp-Leu-Arg-Pro-Cys-Tyr-Asn (SEQ ID NO:20); and

His-Arg-Cys-Gly-Ser-Trp-Leu-His-Pro-Cys-Leu-Ala (SEQ ID NO:21).

14. A separation media consisting of the reaction product of:

(a) an amine-reactive chromatographic matrix material, and (b) a polypeptide selected from the group consisting of:
AEGTGDHPCGSWLRPCLHDPGPEGGGS-NHNH$_2$ (SEQ ID NO:36);

AEGTGDHLCGAWFRPCDADPGPEGGGS-NHNH$_2$ (SEQ ID NO:37); and

Acetyl-AEGTGDHRCGSWLHPCLADPGEGGGSK (SEQ ID NO:44).

15. The separation media of claim 14 wherein said matrix material is an aldehyde-functional methacrylate chromatographic resin.

16. The separation media of claim 15 wherein said resin is a formyl-substituted ethylene glycol-methacrylate copolymer support.

17. A method for separating factor VIII or a fragment of factor VIII, wherein said fragment retains the procoagulant properties of factor VIII, from a solution comprising:

(a) contacting said solution with separation media as defined in claim 12 under binding conditions, and (b) removing unbound material, and (c) eluting bound factor VIII or a fragment of factor VIII, wherein said fragment retains the procoagulant properties of factor VIII, from said separation media.

18. The polypeptide of claim 1 wherein said polypeptide is produced by a recombinant bacteriophage.

19. The polypeptide of claim 2 wherein said polypeptide is produced by a recombinant bacteriophage.

20. A method for detecting human factor VIII or a fragment of human factor VIII, wherein said fragment retains the procoagulant properties of human factor VIII, in a solution comprising:

(a) contacting said solution with the polypeptide of claim 18, and (b) determining whether binding has occurred between said polypeptide and said factor VIII or said fragment of factor VIII.

21. A method for detecting human factor VIII or a fragment of human factor VIII, wherein said fragment retains the procoagulant properties of human factor VIII, in a solution comprising:

(a) contacting said solution with the polypeptide of claim 19, and (b) determining whether binding has occurred between said polypeptide and said factor VIII or said fragment of factor VIII.

* * * * *

SEQUENCE LISTING

<160> NUMBER OF SEQ ID NOS: 46

<210> SEQ ID NO 1
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide
<221> NAME/KEY: VARIANT
<222> LOCATION: (1)..(2)
<223> OTHER INFORMATION: Xaa1 is Arg, Phe, His or Pro; Xaa2 is Ser,
      Gly, Leu or His
<221> NAME/KEY: VARIANT
<222> LOCATION: (4)..(8)
<223> OTHER INFORMATION: Xaa3 is Gly, Asn, Ile or Ser; Xaa4 is Ser,
      Trp or Gly; Xaa5 is Trp, Ile, Leu or Val; Xaa6 is Phe,
      Trp or Ser; Xaa7 is Pro or Phe
<221> NAME/KEY: VARIANT
<222> LOCATION: (10)..(11)
<223> OTHER INFORMATION: Xaa8 is Ser, Leu, Pro or Phe; Xaa9 is Ala,
      Phe, Leu or His

<400> SEQUENCE: 1

Xaa Xaa Cys Xaa Xaa Xaa Xaa Xaa Cys Xaa Xaa
 1               5                  10

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide
<221> NAME/KEY: VARIANT
<222> LOCATION: (1)..(2)
<223> OTHER INFORMATION: Xaa1 is Arg or His; Xaa2 is Ala, Arg, Gly,
      Leu or Pro
<221> NAME/KEY: VARIANT
<222> LOCATION: (4)..(5)
<223> OTHER INFORMATION: Xaa4 is Gly or Phe; Xaa5 is Ala or Ser
<221> NAME/KEY: VARIANT
<222> LOCATION: (7)..(8)
<223> OTHER INFORMATION: Xaa7 is Leu or Phe; Xaa8 is Arg, Asn or His
<221> NAME/KEY: VARIANT
<222> LOCATION: (11)..(12)
<223> OTHER INFORMATION: Xaa11 is Ala, Asp, His, Leu, Phe, Pro or Tyr;
      Xaa12 is Ala, Arg, Asn, Asp or His

<400> SEQUENCE: 2

Xaa Xaa Cys Xaa Xaa Trp Xaa Xaa Pro Cys Xaa Xaa
 1               5                  10

<210> SEQ ID NO 3
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide
<221> NAME/KEY: VARIANT
<222> LOCATION: (3)
<223> OTHER INFORMATION: Xaa3 is His or Trp
<221> NAME/KEY: VARIANT
<222> LOCATION: (5)..(6)
<223> OTHER INFORMATION: Xaa5 is His or Phe; Xaa6 is Ala, Asn, His
      or Pro
<221> NAME/KEY: VARIANT
<222> LOCATION: (8)
<223> OTHER INFORMATION: Xaa8 is Ala, Asn, Asp, Gln, His, Leu, Ser
      or Val
<221> NAME/KEY: VARIANT

```
<222> LOCATION: (11)
<223> OTHER INFORMATION: Xaa11 is Ala, Asp, His, Leu, Phe or Ser

<400> SEQUENCE: 3

Phe Cys Xaa Val Xaa Xaa Phe Xaa His Cys Xaa
 1               5                  10

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 4

His Ser Cys Gly Ser Trp Leu Phe Pro Cys Phe Ala
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 5

Phe Gly Cys Ser Trp Leu Phe Pro Cys Pro Phe
 1               5                  10

<210> SEQ ID NO 6
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 6

Pro His Cys Asn Trp Leu Phe Pro Cys Ser Leu
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 7

Arg Leu Cys Ser Trp Ile Ser Pro Cys Ser Ala
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 8

Phe His Cys Ile Gly Val Trp Phe Cys Leu His
 1               5                  10
```

```
<210> SEQ ID NO 9
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 9

Arg Leu Cys Ser Trp Val Ser Pro Cys Ser Ala
  1               5                  10

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 10

His Pro Cys Gly Ser Trp Leu Arg Pro Cys Leu His
  1               5                  10

<210> SEQ ID NO 11
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 11

Arg Gly Cys Gly Ser Trp Leu Arg Pro Cys Leu Asp
  1               5                  10

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 12

His Pro Cys Gly Ser Trp Leu His Pro Cys Ala Ala
  1               5                  10

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 13

His Pro Cys Gly Ser Trp Phe Asn Pro Cys Ala His
  1               5                  10

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 14
```

```
His Pro Cys Gly Ser Trp Phe Arg Pro Cys Phe His
 1               5                   10
```

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 15

```
His Ala Cys Gly Ser Trp Phe Arg Pro Cys His Ala
 1               5                   10
```

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 16

```
His Leu Cys Gly Ala Trp Phe Arg Pro Cys Asp Ala
 1               5                   10
```

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 17

```
His Leu Cys Phe Ala Trp Phe Arg Pro Cys Asp Ala
 1               5                   10
```

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 18

```
His Gly Cys Gly Ala Trp Phe Arg Pro Cys His Ala
 1               5                   10
```

<210> SEQ ID NO 19
<211> LENGTH: 12
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 19

```
His Pro Cys Gly Ala Trp Phe Asn Pro Cys Pro Arg
 1               5                   10
```

<210> SEQ ID NO 20
<211> LENGTH: 12
<212> TYPE: PRT
<213> ORGANISM: Artificial Sequence

```
<220> FEATURE:
<223> OTHER INFORMATION: Description of Artificial Sequence:  synthetic
      binding loop peptide

<400> SEQUENCE: 20

His Pro Cys Gly Ala Trp Leu Arg Pro Cys Tyr Asn
  1               5                  10

<210> SEQ ID NO 21
<211> LENGTH: 12
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 21

His Arg Cys Gly Ser Trp Leu His Pro Cys Leu Ala
  1               5                  10

<210> SEQ ID NO 22
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 22

Phe Cys Trp Val Phe Ala Phe Asp His Cys His
  1               5                  10

<210> SEQ ID NO 23
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 23

Phe Cys Trp Val His Pro Phe Ala His Cys Leu
  1               5                  10

<210> SEQ ID NO 24
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 24

Phe Cys His Val Phe His Phe Ser His Cys Asp
  1               5                  10

<210> SEQ ID NO 25
<211> LENGTH: 11
<212> TYPE: PRT
<213> ORGANISM: Artificial Sequence
<220> FEATURE:
<223> OTHER INFORMATION: Description of Artificial Sequence:  synthetic
      binding loop peptide

<400> SEQUENCE: 25

Phe Cys Trp Val Phe Ala Phe Asp His Cys His
  1               5                  10
```

```
<210> SEQ ID NO 26
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 26

Phe Cys Trp Val Phe Asn Phe Ser His Cys Ser
 1               5                  10

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 27

Phe Cys Trp Val Phe Pro Phe Asn His Cys Asp
 1               5                  10

<210> SEQ ID NO 28
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 28

Phe Cys Trp Val Phe Pro Phe Asn His Cys Ser
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 29

Phe Cys Trp Val Phe Pro Phe Gln His Cys Ala
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 30

Phe Cys Trp Val Phe Pro Phe His His Cys Phe
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide
```

<400> SEQUENCE: 31

Phe Cys His Val Phe Asn Phe Val His Cys Ser
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: synthetic
      binding loop peptide

<400> SEQUENCE: 32

Phe Cys His Val Phe Pro Phe Leu His Cys Asp
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: template
      for synthetic binding loop peptide
<221> NAME/KEY: VARIANT
<222> LOCATION: (1)..(11)
<223> OTHER INFORMATION: amino acid positions 3 and 9 are invariant
      Cys; all other positions Xaa are varied but not Cys, to
      provide a library of 5x10(9) different peptides
      based on the template sequence

<400> SEQUENCE: 33

Xaa Xaa Cys Xaa Xaa Xaa Xaa Xaa Cys Xaa Xaa
 1               5                  10

<210> SEQ ID NO 34
<211> LENGTH: 12
<212> TYPE: PRT
<213> ORGANISM: Artificial Sequence
<220> FEATURE:
<223> OTHER INFORMATION: Description of Artificial Sequence: template
      for synthetic binding loop peptide
<221> NAME/KEY: VARIANT
<222> LOCATION: (1)..(12)
<223> OTHER INFORMATION: amino acid positions 3 and 10 are invariant
      Cys; all other positions Xaa are varied but not Cys, to
      provide a library of 6x10(9) different peptides
      based on the template sequence

<400> SEQUENCE: 34

Xaa Xaa Cys Xaa Xaa Xaa Xaa Xaa Xaa Cys Xaa Xaa
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: template
      for synthetic binding loop peptide
<221> NAME/KEY: VARIANT
<222> LOCATION: (1)..(11)
<223> OTHER INFORMATION: amino acid positions 2 and 10 are invariant
      Cys; all other positions Xaa are varied but not Cys, to
      provide a library of 5x10(9) different peptides
      based on the template sequence

<400> SEQUENCE: 35

Xaa Cys Xaa Xaa Xaa Xaa Xaa Xaa Xaa Cys Xaa
 1               5                  10

```
<210> SEQ ID NO 36
<211> LENGTH: 27
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 36

Ala Glu Gly Thr Gly Asp His Pro Cys Gly Ser Trp Leu Arg Pro Cys
 1               5                  10                  15

Leu His Asp Pro Gly Pro Glu Gly Gly Gly Ser
             20                  25

<210> SEQ ID NO 37
<211> LENGTH: 27
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 37

Ala Glu Gly Thr Gly Asp His Leu Cys Gly Ala Trp Phe Arg Pro Cys
 1               5                  10                  15

Asp Ala Asp Pro Gly Pro Glu Gly Gly Gly Ser
             20                  25

<210> SEQ ID NO 38
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 38

Ala Glu Gly Thr Gly Asp Phe His Cys Ile Gly Val Trp Phe Cys Leu
 1               5                  10                  15

His Asp Pro Gly Pro Glu Gly Gly Gly Ser
             20                  25

<210> SEQ ID NO 39
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 39

Ala Glu Gly Thr Gly Asp Phe Gly Cys Ser Trp Leu Phe Pro Cys Pro
 1               5                  10                  15

Phe Asp Pro Gly Pro Glu Gly Gly Gly Ser
             20                  25

<210> SEQ ID NO 40
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 40
```

```
Ala Glu Gly Thr Gly Asp Phe Cys Trp Val Phe Ala Phe Asp His Cys
  1               5                  10                  15

His Asp Pro Gly Pro Glu Gly Gly Gly Ser
              20                  25

<210> SEQ ID NO 41
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 41

Ala Glu Gly Thr Gly Asp Phe Cys Trp Val Phe Pro Phe Gln His Cys
  1               5                  10                  15

Ala Asp Pro Gly Pro Glu Gly Gly Gly Ser
              20                  25

<210> SEQ ID NO 42
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 42

Ala Glu Gly Thr Gly Asp Phe Cys Trp Val Phe Pro Phe His His Cys
  1               5                  10                  15

Phe Asp Pro Gly Pro Glu Gly Gly Gly Ser
              20                  25

<210> SEQ ID NO 43
<211> LENGTH: 25
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 43

Ala Glu Gly Thr Gly Asp Arg Leu Cys Ser Trp Val Ser Pro Cys Ser
  1               5                  10                  15

Ala Asp Pro Glu Gly Gly Gly Ser Lys
              20                  25

<210> SEQ ID NO 44
<211> LENGTH: 26
<212> TYPE: PRT
<213> ORGANISM: Artificial Sequence
<220> FEATURE:
<223> OTHER INFORMATION: Description of Artificial Sequence: synthetic
      Factor VIII affinity ligand

<400> SEQUENCE: 44

Ala Glu Gly Thr Gly Asp His Arg Cys Gly Ser Trp Leu His Pro Cys
  1               5                  10                  15

Leu Ala Asp Pro Glu Gly Gly Gly Ser Lys
              20                  25

<210> SEQ ID NO 45
<211> LENGTH: 8
<212> TYPE: PRT
<213> ORGANISM: Artificial Sequence
```

-continued

```
<220> FEATURE:
<223> OTHER INFORMATION: Description of Artificial Sequence: synthetic
      immobilization linker for peptide C-terminus

<400> SEQUENCE: 45

Pro Gly Pro Glu Gly Gly Gly Ser
 1               5

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: synthetic
      immobilization linker for peptide C-terminus

<400> SEQUENCE: 46

Pro Glu Gly Gly Gly Ser Lys
 1               5
```